United States Patent [19]

Angelucci et al.

[11] Patent Number: 5,547,667

[45] Date of Patent: * Aug. 20, 1996

[54] LINKER FOR BIOACTIVE AGENTS

[75] Inventors: Francesco Angelucci; Laura Bersani; Michele Caruso; Marina Ripamonti; Daniela Ruggieri; Antonino Suarato, all of Milan, Italy

[73] Assignee: Farmitalia Carlo Erba S.r.l., Milan, Italy

[ * ] Notice: The term of this patent shall not extend beyond the expiration date of Pat. No. 5,387,578.

[21] Appl. No.: 328,697

[22] Filed: Oct. 25, 1994

Related U.S. Application Data

[63] Continuation of Ser. No. 842,171, Apr. 3, 1992, Pat. No. 5,387,578.

[30] Foreign Application Priority Data

Aug. 3, 1990 [GB] United Kingdom ............... 9017024

[51] Int. Cl.$^6$ ................ A61K 39/44; C07K 17/06; C07K 15/252; C07K 19/06
[52] U.S. Cl. ............ 424/181.1; 514/8; 514/21; 525/54.1; 530/391.1; 530/391.9; 530/399; 530/408; 530/409; 530/345; 536/6.4; 536/22.1; 540/304; 540/350; 540/351; 540/478; 549/298
[58] Field of Search .............. 514/21, 8; 424/181.1; 536/6, 4, 22.1; 530/391.1, 399, 408, 409, 391.9, 345; 540/304, 350, 351, 478; 524/214.1; 549/298

[56] References Cited

U.S. PATENT DOCUMENTS 5,387,578  2/1995  Angelucci et al. ................ 514/21

FOREIGN PATENT DOCUMENTS

| | | |
|---|---|---|
| 211082 | 5/1984 | Czechoslovakia . |
| 0328147 | 8/1989 | European Pat. Off. . |
| 63-241541 | 10/1988 | Japan . |
| 2098219 | 11/1982 | United Kingdom . |
| 8911867 | 12/1989 | WIPO . |
| 9202255 | 2/1992 | WIPO . |

OTHER PUBLICATIONS

Takahashi et al (1984) Iyo Masu Kenkyukai Koenshu 9:77–82.

Webb et al (1990) Polymer Prep. (Am. Chem. Soc., Div. Polym. Chem) 31(2):204–205.

The Journal of Biological Chemistry, vol. 264, No. 25, Sep. 1989, (US) D. M. Neville et al.: "Enhancement of immunotoxin efficacy by acid–clevable cross–linking agents utilizing diphteria toxin and toxen mutants", pp. 14653–14661, see the whole article.

*Primary Examiner*—Kay K. A. Kim
*Attorney, Agent, or Firm*—Oblon, Spivak, McClelland, Maier & Neustadt, P.C.

[57] ABSTRACT

Conjugates of general formula 1:

$$[A—O—W—Z]_a—T \qquad 1$$

wherein the moiety A—O— is the residue of drug of formula A—O—H in which —O—H is a primary or secondary hydroxyl group; a is an integer of from 1 to 30; W is a group of general formula 2:

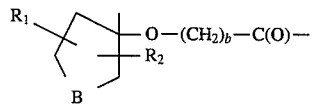

wherein b is an integer of from 1 to 4, B represents a $C_1$–$C_3$ alkylene group and $R_1$ and $R_2$ each independently represent hydrogen, halogen, alkyl, phenyl or substituted phenyl; Z is a spacer group and T is a carrier moiety.

26 Claims, No Drawings

5,547,667

LINKER FOR BIOACTIVE AGENTS

This application is a Continuation of application Ser. No. 07/842,171, filed Apr. 3, 1992, now U.S. Pat. No. 5,387,578, which was filed as International Application No. PCT/EP91/01449 on Aug. 1, 1991.

The present invention relates to conjugates of therapeutically useful anthracyclines with carriers such as polyclonal and monoclonal antibodies or proteins or peptides of natural or synthetic origin; methods for their preparation, pharmaceutical compositions containing them and use thereof in treating certain mammalian tumors. The invention also relates to new anthracycline derivatives and their preparation.

In recent years, many highly cytotoxic anthracyclines have been synthesized. For example, those bearing a morpholino or substituted morpholino ring linked at C-3' position of the sugar moiety have shown promising antitumor activity on experimental murine tumors [see: Bioactive molecules, 55–101, vol 6, Edited by J. William Lown, Elveiser 1988].

The present invention is concerned with new linkers for releasing therapeutically useful drugs from bioactive agents in order to improve the therapeutic efficacy of the drugs and to reduce their toxic effects upon administration in humans. More particularly, the bioactive agents comprise drugs bearing free primary or secondary hydroxyl groups and belonging to therapeutic classes such as antibiotics, antitumorals or antiviral compounds, conjugated to carriers such as antibodies reactive with a selected cell population or to proteins, peptides or polymers of natural or synthetic origin reactive with receptor tissues.

Each drug containing at least a primary or secondary hydroxyl group is covalently bound to the carrier via a linker arm and is bound to that linker arm via an acid-sensitive acetalic bond at its primary or secondary hydroxyl position. The acid sensitive acetalic bond of the bioactive agent of this invention allows the release of active drug in the acidic external or internal environment of the target tissue.

Accordingly the present invention provides conjugates of general formula 1

$$[A-O-W-Z]_a-T \qquad 1$$

wherein the moiety A—O— is the residue of drug of formula A—O—H in which —O—H is a primary or secondary hydroxyl group; a is an integer of from 1 to 30; W is a group of general formula 2:

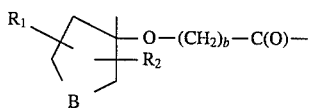

wherein b is an integer of from 1 to 4, B represents a $C_1$–$C_3$ alkylene group and $R_1$ and $R_2$ each independently represent hydrogen, halogen, alkyl, phenyl or substituted phenyl; Z is a spacer group and T is a carrier moiety.

Preferably a is from 1 to 5. B suitably represents —(CH$_2$)$_2$—. In the definition of $R_1$ and $R_2$, halogen is typically chlorine, bromine or iodine and alkyl may be $C_1$–$C_4$ such as methyl or ethyl. Substituted phenyl may be halogen or alkyl-substituted phenyl in which case the halogen and alkyl may be as above. Preferred Z groups are:

(i) —NH—;

(ii) —NH—(CH$_2$)$_c$—S—S— wherein c is an integer of from 1 to 4;

(iii) —NH—[C]$_d$—N=CH— wherein:

a) d is 0, b) d is 1 and [C] represents —NH—CO(CH$_2$)$_e$—CO—NH— in which e is an integer of from 2 to 4, c) d is an integer of from 1 to 4 and [C] represents —(CH$_2$)$_f$—O—(CH$_2$)$_f$— in which f is 1 or 2, or d) d is an integer of from 2 to 6 and [C] is CH$_2$;

(iv) —NH—[C]$_d$—NH—CO— wherein [C] and d are as defined above;

(v) —[D]—NH— wherein [D] represents —NH—[CH$_2$]$_g$—CO— in which g is an integer of from 2 to 6;

(vi) —[E]—CO— wherein [E] represents —NH—(CH$_2$)$_g$—NH— in which g is an integer of from 2 to 6 or (vii) the piperazinylcarbonyl moiety of formula:

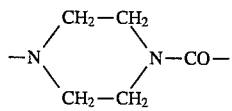

In the above formula 1 the drug A—O—H preferably represents an antitumor agent belonging to the class of anthracyclines such as doxorubicin, its 3'-deamino-3'-morpholinyl derivatives in which the morpholino ring optionally is substituted at position 2" with alkoxy residues such as a $C_1$–$C_4$ alkoxy group; pyrimidine analogs such as 5-fluorodeoxyuridine or arabinofuranosylcytosine (cytarabine); derivatives of vinca alkaloids such as 4-desacetylvinylblastine; or other antitumor agents such as podophyllotoxin or illudines. Alternatively, the drug A—O—H may be an antiviral agent such as 3'-azido-3'-deoxythymidine (AZT), bromovinyldeoxy-uridine (BVDU), 9-[(2-hydroxyethoxy)methyl]guanine (acyclovir) or 9-[(1,3-dihydroxy-2-propoxy)methyl]guanine (gancyclovir) or an antibiotic such as thienamycin or our new penem derivatives such as (5R,6S)-2-carbamoyloxymethyl-6-[(1R)-hydroxyethyl]-2-penem-3-carboxylic acid and acetoxymethyl (5R,6S)-2-carbamoyloxymethyl-6-[(1R)-hydroxyethyl]-2-penem-3-carboxylate.

When the moiety A—O— is derived from an anthracycline A—O—H typically the moiety A—O— represents

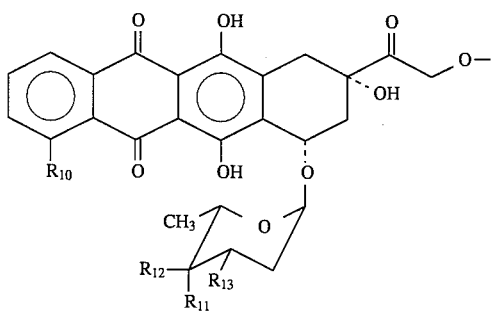

in which $R_{10}$ is a hydrogen atom or a hydroxy or methoxy group, one of $R_{11}$ and $R_{12}$ is a hydrogen atom and the other is a hydroxy group or $R_{11}$ is a hydrogen or iodine atom and $R_{12}$ is a hydrogen atom, and $R_{13}$ is an amino group or represents a nitrogen atom enclosed in a morpholino ring. The morpholino ring may be for example a morpholino (MO), 3-cyano-4-morpholino (CM) or 2-methoxy-4-morpholino (MM) ring in which the nitrogen atom is linked at C-3' as follows:

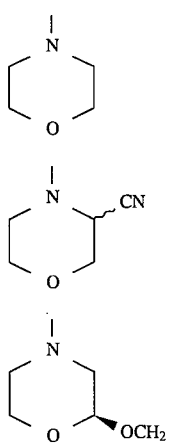

(MO)

(CM)

(MM)

The carrier moiety T is typically selected from a polyclonal antibody, or fragment thereof comprising an antigen binding site, capable of binding to a tumor associated antigen; a monoclonal antibody, or fragment thereof comprising an antigen binding site, capable of binding to an antigen preferentially or selectively expressed on tumor cell populations; a peptide or protein capable of preferentially or selectively binding to a tumor cell; and a polymeric carrier.

The carrier moiety, preferably a carrier moiety derived from a substance which may be represented as $T-[NH_2]_x$ where x represents the number of amino groups available for condensation, can be selected from polyclonal antibodies raised against tumor associated antigens; or from monoclonal antibodies binding to antigens preferentially or selectively expressed on tumor cell populations; or from natural or recombinant peptides or proteins or growth factors preferentially or selectively binding to tumor cells; or from natural or synthetic polymeric carriers such as polylysine. The carrier portion may be also derived from portions of the above mentioned carriers, such as the Fab or the $F(ab')_2$ fragments of the antibodies, or from portions of the above mentioned peptides or proteins obtained through recombinant DNA techniques.

Representative examples of the above mentioned antibodies and of respective possible therapeutic applications are:

— anti-T-cell antibody such as antibody T101 [Royston, I. et al., J. Immunol. 1980, 125, 725]
— anti-CD5 antibody such as antibody OKT1 (Ortho) ATCC CRL 8000 (chronic lymphocytic leukaemias)
— anti-trasferrin receptor antibody such as antibody OKT9 (Ortho) ATCC CRL 8021 (ovaric and other tumors)
— anti-melanoma antibody such as antibody MAb 9.2.27 (Bumol, T. F. et al., Proc. Natl. Acad. Sci. USA 1982, 79, 1245) (melanomas)
— Anti-carcinoma marker antibodies such as:
—anti-CEA 1116 NS-3d ATCC CRL 8019
—anti alpha-fetoprotein OM 3-1.1 ATCC HB 134 (also hepatomas)
—791T/36 [Embleton, M. J. et al., Br. J. Cancer 1981, 43, 582] (also osteogenic sarcoma)
—B 72.3 [U.S. Pat. No. 4,522,918 (1985)] (colorectal carcinomas and other tumors)
— anti-ovarian carcinoma antibody such as antibody OVB 3 ATCC HB 9147
— anti-breast carcinoma antibody such as antibody (HMGF antigen) [Aboud-Pirak, E. et al., Cancer Res. 1988, 48, 3188]
— anti-blader carcinoma antibody such as antibody 1G3.10 [Yu, D. S. et al., Eur. J. Urol. 1987, 13, 198]

Representative examples of the above mentioned growth factors and proteins of natural or recombinant origin are FGF, EGF, PDGF, TGF-$\alpha$, $\alpha$-MS, interleukines, interferons, TNF melanotropin (MSH), etc.

A carrier moiety derived from a substance which may be represented as $T-[SH]_{x1}$ wherein x1 denotes the number of thiol groups available for condensation, is preferably derived from thiolated polyclonal or monoclonal antibodies obtained using e.g. N-succinimidyl-S-acetylthioacetate (SATA), N-succinimidyl-3-(2-pyridylthio)propionate (SPDP), D,L-homocysteine thiolactone, N-acetyl-D,L-homocysteine thiolacetone or 2-iminothiolactone.

A carrier moiety derived from a substance which may be represented as $T-[CHO]_{x2}$, wherein x2 denotes the total number of formyl groups available for condensation, is preferably derived from polyclonal or monoclonal antibodies having the carbohydrate moiety, preferentially located in the Fc region, selectively oxidized to aldehyde groups by means of chemical or enzymatic methods, as described in U.S. Pat. No. 4,671,958. A carrier $T-[CHO]_{x2}$ may be also derived from the formylation or from the oxidation of suitable polymeric carriers, or from the oxidation to aldehyde groups of the carbohydrate residues of suitable glycoproteins.

A carrier moiety derived from a substance which may be represented as $T-[COOH]_{x3}$, wherein x3 denotes the total number of carboxyl groups available for condensation, is preferably derived from polyaspartic or polyglutamic acid or from soluble and biodegradable synthetic copolymers such as those derived from N-(2-hydroxypropyl)methacrylamide (HMPA) having the following structure:

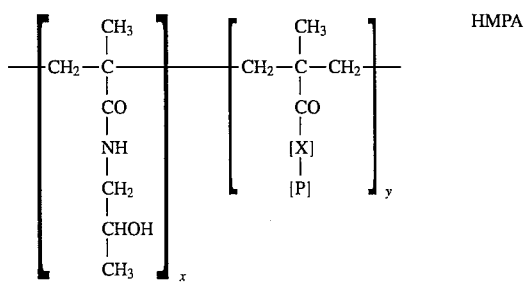

[X]: —Gly-Phe-Leu-Gly; —HN—$(CH_2)_n$—CO; n from 1 to 5. [P]: OH, O—$C_6H_4pNO_2$ x/y (90/10+95/5 mol/mol %); MW 10000–40000, preferably 12000–20000 [see: J. Kopecek, "Biodegradation of polymers for biomedical use" in IUPAC Macromolecules. H. Benoit & P. Rempp, Ed.: 505–520 (1982) Pergamon Press. Oxford, England] or from poly (amino acid) copolymers such as poly (GluNa,Ala,Tyr) or $M_w$ 25000–50000 daltons that are useful as targetable drug-carriers for lung tissue (below) [R. Duncan et al., see Journal of Bioactive and Compatible Polymers, Vol 4, July 1989] or from the carboxylic groups naturally present on monoclonal or polyclonal antibodies or chemically introduced by treatment of the antibody with bifunctional anhydrides (e.g. maleic anhydride).

Structure of poly (GluNa, Ala, Tyr) copolymer

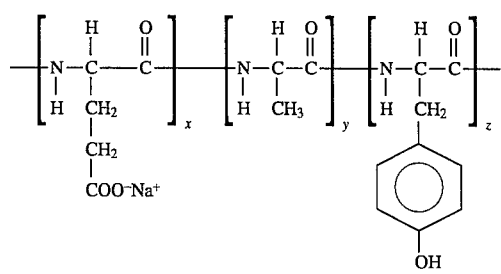

x:y:z: = 1:1:1

The invention further provides a process for preparing a conjugate of formula 1, which process comprises: condensing a derivative of formula 3,

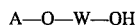     3 wherein A—O— and W are as above defined, with a substance or substances which is or are able to provide the said spacer group Z and carrier moiety T in the said conjugate of formula 1, thereby forming the said conjugate of formula 1.

The condensation may be carried out via an activated derivative such as a mixed anhydride, an azide or an activated ester of the derivative of the formula 3 or by direct reaction in the presence of a condensing agent such as dicyclohexylcarbodiimide. A suitable process comprises converting the derivative of formula 3 into an activated derivative of formula 4

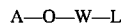     4 wherein A—O— and W have the same meanings as above and L represents an activating group for making an amidic linkage, such as N-oxysuccinimido, its water soluble derivative N-oxysulfosuccinimido or a 2,4-dinitrophenoxy, 2,3,4,5,6-pentafluorophenoxy or t-butoxy carbonyloxy group; and (i') condensing the resultant compound of formula 4 with a substance of formula T—[NH$_2$]$_x$ as previously defined to afford a bioactive agent of the formula 1 having amidic linkage(s), or (ii') condensing the compound of formula 4 with a thiol derivative of formula NH$_2$—(CH$_2$)$_c$—SH, such as 2-aminoethanethiol in which C=2, and condensing the resultant compound of formula 5:

     5 wherein A—O—, W and C are as above defined, with a substance of formula T—[SH]$_{x1}$ as previously defined to give a conjugate of formula 1 having disulfide linkage(s); or (iii') reacting the compound of formula 4 with hydrazine, a succinic or adipic dihydrazide derivative or a diamino compound and condensing the resultant compound of formula 6:

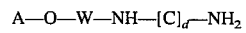     6 wherein A—O—, W, [C] and d are as above defined, with a substance of formula T—[CHO]$_{x2}$ as previously defined to give a bioactive agent of formula 1 having oxime linkage(s).

A useful process comprises (iv') condensing a compound of general formula 6, as above described, with a substance of formula 7,

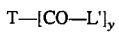     7 which is derived from a reaction involving a carrier of formula T—[COOH]$_{x3}$ as above defined and in which y is an integer of from 1 to 30 and represents the total number of activated carboxyl groups, T is the carrier moiety in the resulting conjugate of formula 1 and L', represents a hydroxy or an activating group for making an amide linkage, optionally in the presence of a condensing agent to give a conjugate of formula 1, in which the unreacted optionally present activated carboxyl groups may be quenched with a pharmaceutically acceptable amine such as 1-amino-2-propanol.

Other useful processes comprise (v') condensing a compound of formula 4 with an amino derivative of formula H$_2$N—[CH$_2$]$_g$—COOH in which g is as above defined, thereby to form a derivative of formula 8:

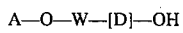     8 wherein A—O—, W and [D] are as above defined; optionally converting the compound of formula 8 into an activated derivative of formula 9:

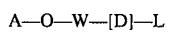     9 wherein A—O—, W, [D] and L are as above defined, and condensing the resultant compound of formula 9 or a compound of formula 8 in the presence of a condensing agent with a substance of formula T—[NH$_2$]$_x$ as previously defined to afford a bioactive agent of the formula 1.

Other processes comprise (vi') reacting a compound of formula 4 with an amino derivative of formula H$_2$N—(CH$_2$)$_g$—NH$_2$ in which g is as above defined, thereby to form a derivative of formula 10:

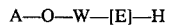     10 wherein [E] is as above defined or (vii') reacting a compound of formula 4 with piperazine to form a derivative of formula 11:

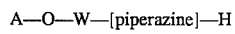     11 and condensing a compound of formula 10 or 11, as above described, with a substance of formula 7 as previously described to give a conjugate of formula 1.

For example, an activation method for the conversion of a compound of formula 3 or 8 into a derivative 4 or 9 is the reacting of the compound of formula 3 or 8 with N-hydroxysuccinimide or its water soluble 3-substituted sodium sulfonate salt in the presence of N,N'-dicyclohexylcarbodiimide in a solvent such as ethyl acetate or N,N-dimethylformamide. In such a case in formula 4 and 9, L represents the residue:

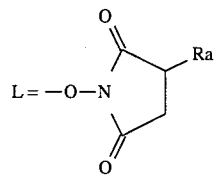

wherein R$_a$ represents hydrogen atom or sodium sulphate group.

An activation method for converting carriers of type T—[COOH]$_{x3}$ into compounds of general formula 7 is the reaction of such a carrier with p-nitrophenol in the presence of N,N'-dicyclohexylcarbodiimide in a solvent such as dimethylformamide, in which case L' represents $pNO_2C_6H_5$—O— or with N-ethoxycarbonyl-2-ethoxy-1,2-dihydroquinone (EEDQ) [see: B. Belleau et al., JACS, 90 1651 (1968)] in a solvent such as tetrahydrofuran or dimethylformamide, in which case in formula 7 L' represents the residue:

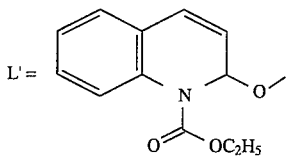

Another procedure comprises reacting an alkaline salt of the carrier T—$[COOH]_{x3}$, such as the sodium salt, with an alkyl-halo-carbonate such as a ($C_1$–$C_4$)alkyl-halo-carbonate, preferably ethyl chloro carbonate ($C_2H_5O$—COCl), in a solvent such as water or dimethylformamide. In that case in formula 7 residue L' represents —$COOC_2H_5$.

The condensation methods for preparing conjugates of formula 1, starting from a derivative of formula 3 or 8 and a carrier of formula T—$[NH_2]_x$, are carried out in conditions capable of creating covalent linkages of amidic type and compatible with the structure of the carrier. According to the chemical stability of the carrier in aqueous or organic solvents, different procedures may be employed for the coupling reaction with intermediates of general formulae 4, 5, 6, 9, 10 and 11. For carriers sensitive to organic solvents, preferred conditions encompass use of buffered aqueous solutions at pH 7–9.5, temperatures of 4°–37° C., for times from some hours to several days.

Methods for preparing conjugates of formula 1 by condensing a derivative 5 with a carrier of formula T—$[SH]_{x1}$ are carried out in conditions which encompass the use of buffered aqueous solutions at pH 6–7, temperature of 4° C., for times from some hours to several days.

Methods for preparing conjugates of formula 1 by condensing a derivative 6 with a carrier of formula T—$[CHO]_{x2}$ are carried out in conditions capable of creating covalent linkages of the oxime or hydrazone type and compatible with the structure of the carrier. Preferred conditions encompass use of buffered aqueous solutions at pH 4–7.5, temperature of 4°–37° C., for times from some hours to several days.

Methods for preparing conjugates of formula 1 by condensing a derivative 6, 10 or 11 with a carrier of formula T—[CO—L']$_y$, are carried out in conditions capable of creating covalent linkages of the amidic type and compatible with the structure of the carrier. Preferred conditions encompass use of buffered aqueous solutions at pH 7–9.5, temperature of 4°–37° C., for times from some hours to several days.

Other conditions encompass the use of dry dimethylsulfoxide or dimethylformamide at room temperature for 1 to 3 hours.

Herein, the period "from some hours to several days" may be from 4 hours to 5 days.

For example, suitable conditions for the condensation between the compounds of formulae 4 and 9 and antibodies T—$[NH_2]_x$ are: aqueous 0.1M sodium phosphate and aqueous 0.1M sodium chloride at pH 8 containing a monoclonal antibody at 1 mg/ml, treated with a 30 fold molar excess of 10% w/v solution of 4 or 9 in N,N-dimethylformamide, for 24 hours at 20° C. The conjugate is purified by gel filtration on a Sephadex G-25 column (Pharmacia Fine Chemical, Piscataway, N.H.), eluting with PBS (Phosphate-buffered saline).

Suitable conditions for the coupling between the compounds of formula 5 and functionalized antibodies bearing thiol groups are: aqueous 0.1M sodium acetate and aqueous 0.1M sodium chloride at pH 6 containing a monoclonal antibody at 1 mg/ml, treated with a 30 fold molar excess of a 5% w/v solution of 5 in the same buffer, for 24 hours at 4° C. The conjugate is purified by gel filtration as above described.

Suitable conditions for the coupling between the compounds of formula 6 and carriers of type T—$[CHO]_{x2}$ are: aqueous 0.1M sodium acetate and aqueous 0.1M sodium chloride at pH 6–7 containing a monoclonal antibody at 1 mg/ml, treated with a 30 fold molar excess of a 5% w/v solution of 6 in the same buffer, for 24 hours at 20° C. The conjugate is purified by gel filtration as above described.

Suitable conditions for the condensation between the compounds of formulae 6, 10 and 11 and an activated carrier of formula 7 are: anhydrous polar solvent such as dimethylformamide containing 5 to 50 mg/ml of compound 6, 10 or 11, treated with an equivalent amount of compound 7, for 1 to 24 hours at 20° C.

The compounds of general formula 3 as well as the activated compounds of formula 4, 5, 6, 9, 10 and 11 are novel and therefore are within the scope of the present invention.

The compounds 3, 5, 6, 10 and 11 are both useful intermediates and/or therapeutically active agents. More particularly, intermediates of general formula 3 are useful prodrugs of compounds of general formula A—O—H, previously described. The derivatives of formula 3 can be prepared by the process illustrated in Chart 1. This process comprises condensing a drug of formula A—O—H with a suitable enol ether derivative bearing a masked carboxy group, such as one of formula 12:

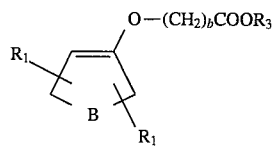

wherein B, b, $R_1$ and $R_2$ are as previously defined and $R_3$ represents a protecting group, such as methyl or ethyl; and removing the protecting group from the resultant compound.

Chart 1

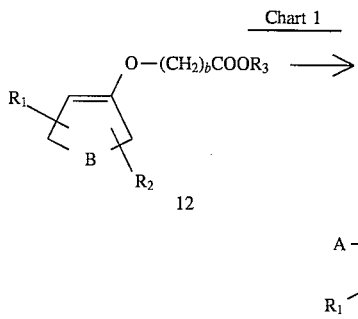

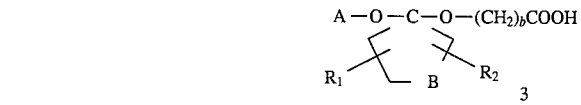

Without limiting the invention, the antitumor anthracyclines represent suitable hydroxylated drugs (A—OH) for making bioactive derivatives of general formula 1. Among the class of anthracycline, 3'-deamino-3'-morpholinyl derivatives of general formula (13) such as 3'-deamino-3'-(4 -morpholinyl)doxorubicin (13a) or 3'-deamino-3'-(2-methoxy-4 -morpholinyl)doxorubicin (13b) [see: E. M. Acton et al; Morpholinyl Anthracyclines, in Bioactive Molecules, Vol 6, Edt.

by J. W. Lown, Elsevier, 1988] represent the compounds of choice.

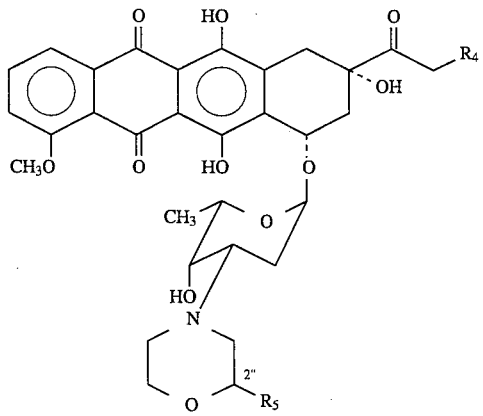

A—OH = 13a: $R_4$ = OH, $R_5$ = H
A—OH = 13b: $R_4$ = OH, $R_5$ = $OCH_3$
A—O— = 13a': $R_4$ = O—, $R_5$ = H
A—O— = 13b': $R_4$ = O—, $R_5$ = $OCH_3$

The conversion of anthracyclines of formula 13a,b into new acid-sensitive derivatives of general formula 3 as above defined, may be carried out by treatment with a compound formula 12, previously illustrated, in which Rx is a residue such as ethyl group, prepared as described by J. A. Landgrebe et al in J. Org. Chem 43, 1244 (1978) by reacting a suitable compound bearing a ketone group with ethyl diazoacetate. Preferred conditions for carrying out the reaction of anthracyclines, as well as other compounds having primary or secondary hydroxyl groups with compound 12 encompass the use of a sulfonic acid catalyst such as p-toluensulfonic acid or camphorsulfonic acid, in polar solvent such as dimethylformamide, at room temperature for times from some hours to one day. The masked carboxyl group of the acid-sensitive moiety linked to the anthracyclines in compounds of formula 3 is converted into activated carbonyl group of compounds of formula 4 from which the new bioactive agents are prepared via coupling with suitable carriers Optionally, anthracycline derivatives of general formula 4 might be converted into derivatives of general formula, 5, 6, 8, 9, 10 and 11 and reacted with suitable carriers for making new bioactive agents of general formula 1. Also therapeutically useful drugs, such as those previously described, can be reacted with compounds of formula 12, in the same fashion as described for anthracyclines and converted into bioactive agents for the cure of certain mammalian diseases.

The bioactive agents of formula 1 of the present invention are useful therapeutic agents since they contain an acetalic bond which releases the parent drug A—OH upon hydronium-ion-catalyzed hydrolysis or "in vivo" enzymatic cleavage. For instance, it is well known that in malignant tumors there is a high rate of glycolysis compared to normal tissue. This causes an increase in the production of lactate and thus a decrease of the pH in the tumor [see: H. M. Rauen et al., Z. Naturforsch, Teil B, 23 (1968) 1461]. The conjugates produced according to the methods described are characterized following different chemico-physical methods. For instance, the retention of the original molecular weight and the lack of aggregate formation is assessed by chromatographic gel filtration procedures (Yu, D. S. et al., J. Urol. 140, 415, 1988) with simultaneous and independent detection of anthracycline and antibody at different wavelengths and by gel electrophoretic methods. The overall charge distribution of the compounds obtained is assessed by chromatographic ion exchange methods. The anthracycline concentration is assessed by spectrophotometric titration against a standard calibration curve obtained from the parent anthracycline. The protein concentration is assessed by colorimetric assays such as the bicinconic acid assay (Smith, P. K. et al., Anal. Biochem. 150, 76, 1985) or the Bradford dye assay (Bradford, M. M., Anal. Biochem. 72, 248, 1976). The antigen binding activity retention of the antibodies, after the conjugation procedures, is assessed by an ELISA method (Yu, D. S. et al., J. Urol. 140, 415, 1988) and by cytofluorimetric methods (Gallego, J. et al., Int. J. Cancer 33, 737, 1984). The evaluation of the retention of cytotoxicity of conjugates in comparison with the parent drug is assessed by a test of inhibition of uptake of $^3$H-Thymidine by the target cells, after an incubation time long enough to explicate the maximum cytotoxic effect (Dillmann, R. O. et al., Cancer Res. 48, 6097, 1988).

The evaluation of selective cytotoxicity of the conjugates toward an antigen positive in comparison with an antigen negative cell line is assessed by a test of inhibition of uptake of $^3$H-Thymidine by antigen positive vs. antigen negative cell lines, after a short incubation time (Dillmann, R. O. et al., Cancer Res. 48, 6096, 1988).

The acid sensitivity of the conjugate is evaluated by the above mentioned chromatographic methods after incubation of the compounds in suitable buffered solutions.

Alternatively, radiolabelling of the conjugates in the antibody moiety ($^{225}$I) and/or in the anthracycline moiety ($^{14}$C) and HPLC analytical methods are employed for the evaluation of stability in plasma.

BIOLOGICAL ACTIVITY

Compound 3' (prepared in example 1) was tested in vitro' against LoVo (human colon adenocarcinoma) and LoVo-Doxo-resistant (LoVo/DX) cells in comparison with Doxorubicin and 3'-deamino-3'-[2(S)-methoxy-4-morpholinyl] doxorubicin (13b), using a single cell plating technique after 4 hours treatment (Colony assay). The 50% inhibition concentration ($IC_{50}$) was calculated on concentration-response curves. Data reported in Table 1 show that compound 3' is more cytotoxic than doxorubicin, both on sensitive and resistant cell lines, but 15–20 times less cytotoxic than its parent compound 13b. Compound 3 was treated in vivo in CDF-1 mice bearing P388 -doxorubicin-resistant leukemia (P388/DX Johnson) in comparison with doxorubicin and compound 13b. Data reported in Table 2 show that compound 3', administered ip on day 1 after the tumor inoculation, at 0.22 mg/kg is very active (T/C % 184).

Conjugates of formula 1', 1", 1$^v$, 1$^{vi}$, and 1$^{vii}$ (prepared respectively in examples 5, 6, 9, 11 and 12) in which the residue of the cytotoxic drug 3'-deamino-3'[2(S)-methoxy-4-morpholinyl]doxorubicin is linked through an acidic sensitive linker, were tested in vivo on P388/DX Johnson leukemia in comparison with doxorubicin and the free drug 13b. Data reported in Table 3 show that all the new compounds, administered iv on day 1 after the tumor inoculation maintain activity equal to that of the free drug 13b. The therapeutic index, expressed as the ratio between the $LD_{50-100}$ and the optimal dose, is higher in all the conjugates vs. the free drug 13b.

In Table 4 are reported $t_{50\%}$ of release of 3'deamino-3' [2(S)-methoxy-4-morpholinyl]doxorubicin (13b) from the conjugates at pH 3 (acetate buffer) at 37° C.

TABLE 1

Cytotoxicity after 4 hr treatment. $IC_{50}$ = ng/ml[1].

| Compound | LoVo $ID_{50}$ (ng/ml) | LoVo/DX $ID_{50}$ (ng/ml) | R.I.[2] |
|---|---|---|---|
| Doxorubicin | 60 | 2180 | 36.3 |
| 13b | 16 | 33 | 2 |
| 3' | 240 | 745 | 3 |

[1] $IC_{50}$ = concentration inhibiting by 50% colony growth.
[2] R.I. = Resistance Index = ($IC_{50}$ LoVo/DX)/($IC_{50}$ LoVo)

TABLE 2

Antitumor activity against P388/DX Johnson leukemia, treatment ip on day 1

| Compound | Dose (mg/kg) | T/C[3] % | Toxic[4] deaths |
|---|---|---|---|
| Doxorubicin | 10 | 100 | 0/10 |
|  | 15 | 100 | 0/10 |
|  | 22 | 100 | 10/10 |
| 13b | 0.1 | 136 | 0/10 |
|  | 0.125 | 155 | 1/10 |
| 3' | 0.22 | 184 | 0/10 |

[3] Median survival time; % over untreated controls.
[4] Evaluated on the basis of autopsy findings on dead mice.

TABLE 3

Antitumor activity against P388/DX Johnson leukemia, treatment iv on day 1

| Compound | Dose[5] (mg/kg) | T/C[3] % | Toxic[4] deaths |
|---|---|---|---|
| Doxorubicin | 16.9 | 105 | 0/10 |
|  | 22 | 100 | 3/10 |
| 13b | 0.076 | 177 | 0/28 |
|  | 0.09* | 192 | 0/39 |
| 1' | 0.16 | 144 | 0/10 |
|  | 0.25* | 175 | 0/20 |
|  | 0.5 | 167 | 0/10 |
| 1" | 0.16 | 156 | 0/10 |
|  | 0.25* | 200 | 0/10 |
|  | 0.5 | 133 | 0/10 |
| 1ᵛ | 0.25 | 111 | 0/10 |
|  | 0.5 | 144 | 0/10 |
|  | 1* | 205 | 0/20 |
|  | 1.25 | 200 | 0/10 |
| 1ᵛⁱ | 0.66 | 172 | 0/10 |
|  | 1* | 194 | 0/10 |
| 1ᵛⁱⁱ | 0.66* | 233 | 0/10 |
|  | 1 | 177 | 0/10 |

*Optimal Dose
[5] Dose: (ng/Kg): expressed as content of 13b in the conjugate.

TABLE 4

Release of 13b from conjugates at pH 5 and temperature 37° C. in acetate buffer[7].

| Compound | $t_{50\%}$[6] (hours) |
|---|---|
| 1' | 2.5 |
| 1" | 3.5 |
| 1ᵛ | 24 |
| 1ᵛⁱ | 22 |
| 1ᵛⁱⁱ | 20 |
| 1ᵛⁱⁱⁱ | 3.5 |

[6] Time requests for the release of 50% of free drug 13b. Determined by HPLC using a calibration curve of compound 13b.
[7] Ionic strength 0.05M.

The therapeutic effect of the compounds and the improvement of their therapeutic efficacy in comparison with the parent are assessed in animal models of human trasplanted tumors. Nude mice bearing xenografts of human tumors are treated with suitable doses of conjugates, of free drug, of antibody, and of a physical mixture of drug and antibody, at equivalent doses, and the tumor growth is recorded and compared in the different treatment groups.

The conjugates are formulated as pharmaceutical compositions with an pharmaceutically acceptable carrier or diluent. Any appropriate carrier or diluent may be used. Suitable carriers and diluents include physiological saline solution and Ringers dextrose solution.

The following Examples illustrate the invention without limiting it.

EXAMPLE 1

Preparation of 14-O-(1-carboxymethyloxy-cyclohexyl)-3'-deamino-3'-[2(S)-methoxy-4-morpholinyl]doxorubicin [3': A—O—=13b', b=1, B=—(CH₂)₂—, R₁=R₂=H]

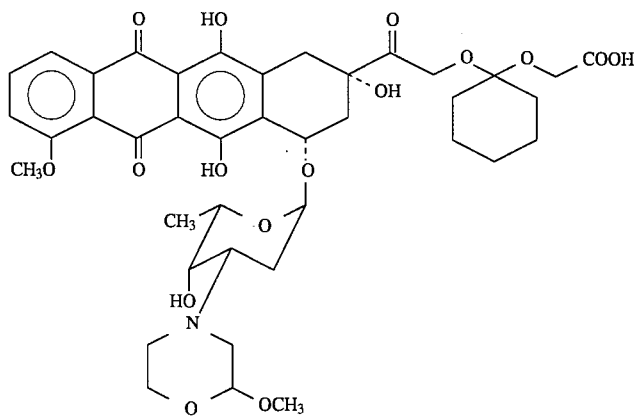

3'-deamino-3'-[2(S)-methoxy-4-morpholinyl]doxorubicin (13b) (0.68 g, 1 mmole), prepared as described in WO-A-91/09046, was dissolved in anhydrous dimethylformamide (20 ml) and treated with ethyl 2-(cyclohexen-1-yl)-oxy acetate [12'; b=1, $R_3=C_2H_5$, B=—$(CH_2)_2$—, $R_1=R_2=H$] (6 g, 32 mmole) in presence of melted p-toluenesulfonic acid (50 mg). The mixture was stirred for two hrs at room temperature, after that, was poured into aqueous sodium hydrogen carbonate and extracted with methylene chloride. The organic phase was washed with water, dried over anhydrous sodium sulphate and filtered. The solvent was removed under reduced pressure and the residue was chromatographed on flash silicic acid column using as eluting system a mixture of methylene chloride/methanol (98/2 by volume) to give the ester derivative ($R_3=C_2H_5$) of the title compound 3'.

This was treated with aqueous 0.1N sodium hydroxide (200 ml) at 0° C. under stirring and in presence of nitrogen for 1 hr. After that, the mixture was brought to pH 8.2 with acetic acid and extracted with n-butanol. The organic phase was washed with water, concentrated to small volume under reduced pressure and chromatographed on silicic acid column using as eluting system a mixture of methylene chloride/methanol (80/20 by volume) to give the title compound 3' (0.35 g, yield 43%) as free acid derivative which was treated with an equivalent amount of aqueous hydrochloric acid and lyophilized.

TLC on Kieselgel Plate (Merck) $F_{254}$, eluting system methylene chloride/methanol (95/5 by volume), $R_f$=0.13
MS-FD: m/e 783 (M+).

$^1$NMR (200 MHz, DMSO $d_6$) δ: 1.12 (d, J=6.4Hz, 3H, C$\underline{H}_3$-5'); 1.3–1.9 (m, 12H,

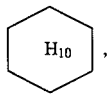

C$\underline{H}_2$ -2'); 2.0–2.7 (m, 7H, C$\underline{H}_2$-8, O—CH$_2$C$\underline{H}_2$—N, O—CH—C$\underline{H}_2$—N, $\underline{H}$-3'); 2.94 (s, 2H, C$\underline{H}_2$-10); 3.24 (s, 3H, CH—OC$\underline{H}_3$); 3.40, 3.73 (two m, 2H, NCH$_2$C$\underline{H}_2$O); 3.57 (m, 1H, $\underline{H}$-4'); 3.91 (s, 2H, OC$\underline{H}_2$COOH); 3.97 (s, 3H, O C$\underline{H}_3$-4); 4.04 (dq, J=6.4, 1.0Hz, 1H, $\underline{H}$-5'); 4.35 (dd, J=2.2, 5.2Hz, 1H, OC$\underline{H}$—OCH$_3$); 4.61 (s, 2H, C$\underline{H}_2$-14); 4.92 (m, 1H, $\underline{H}$-7); 5.24 (m, 1H, $\underline{H}$-1'); 7.6–7.9 (m, 3H, $\underline{H}$-1, $\underline{H}$-2, $\underline{H}$-3); 13.20 (bs, 1H, O$\underline{H}$-11); 14.02 (s, 1H, O$\underline{H}$-6).

EXAMPLE 2

Preparation of N-oxysuccinimidyl derivative of 14-O-(1-carboxymethyloxy-cyclohexyl)- 3'-deamino-3'-[2(S)-methoxy-4-morpholinyl]doxorubicin [4'; A—O—=13b', b=1, B=—$(CH_2)_2$—, $R_1=R_2=H$,

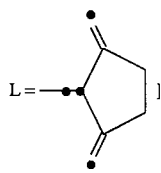

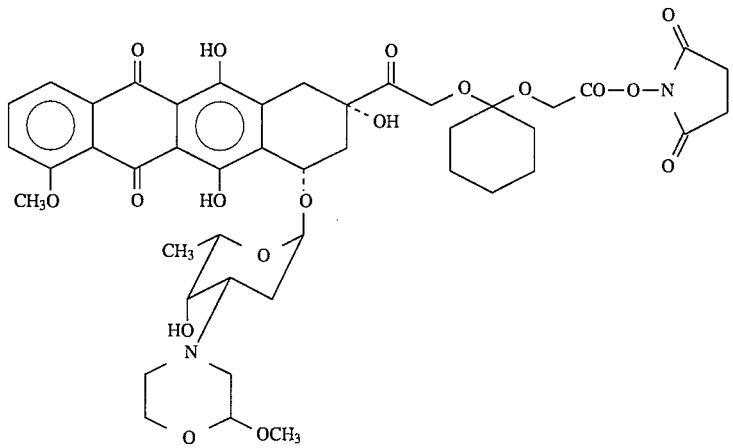

Compound 3' (0.2 g, 0.25 mmole), prepared as described in Example 1, was dissolved in anhydrous dimethylformamide (8 ml), cooled at 0° C. and treated with N-hydroxysuccinimide (0.2 g) and dicyclohexylcarbodiimide (0.4 g). The mixture was kept at 0° C. for two hrs and then was left at room temperature overnight. After that, the mixture was concentrated to small volume under reduced pressure and chromatographed on flash silicic acid column using as eluting system a mixture of methylene chloride/methanol (97/3 by volume). The eluate containing the title compound was concentrated to dryness under reduced pressure, then the residue was taken up in ethyl acetate, filtered and concentrated to small volume under reduced pressure. Finally, ethyl ether was added and the title compound 4' (0.130 g) was collected on sintered glass funnel, washed with ethyl ether and stored under nitrogen.

TLC on Kieselgel Plate (Merck) $F_{254}$, eluting system methylene chloride/methanol (95/5 by volume) $R_f$=0.37 MS-FD: m/e 864 (M+).

EXAMPLE 3

Preparation of 14-O-(1-hydrazinocarbonylmethyloxy-cyclohexyl)-3'-deamino-[2(S)-methoxy-4-morpholinyl]doxorubicin [6', A—O—=13b', b=1, B=—$(CH_2)_2$—, $R_1$=$R_2$=H, C=0]

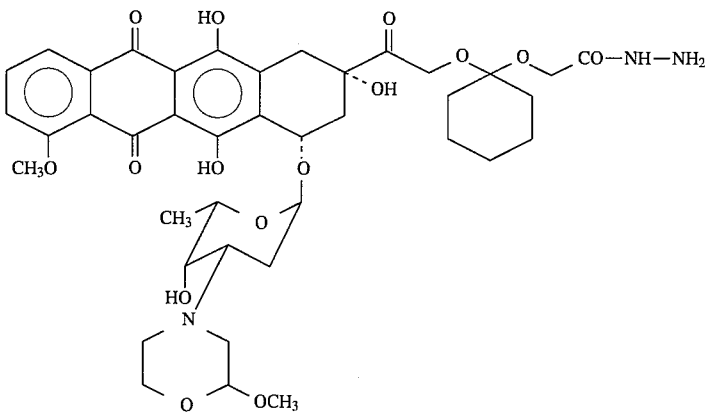

Compound 4' (20 mg), prepared as described in Example 2, was dissolved in tetrahydrofuran (5 ml) and added with 1M solution of hydrazine hydrate in isopropanol. The mixture was kept at 0° C. for 70 minutes. After that, methylene chloride was added and the mixture was washed three times with cold water. The organic layer was separated, dried over anhydrous sodium sulphate, filtered and the solvent removed under vacuum. The residue was chromatographed on silicic acid column using as eluting system a mixture of methylene chloride/methanol (99/1 by volume). Compound 6', 20 mg, was precipitated with ethyl ether.

TLC on Kieselgel Plate (Merck) $F_{254}$, eluting system methylen chloride/methanol (95/5 by volume) $R_f$=0.25 MS-FD: m/e 797 (M+).

$^1$NMR (200 MHz, DMSO $d_6$) δ: 1.36 (d, J=6.6Hz, 3H, C$\underline{H}_3$-5'); 1.4–1.7 (m, 10H,

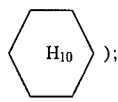

1.76 (m, 2H, C$\underline{H}_2$-2'); 2.30 (m, 2H, C$\underline{H}_2$-8); 2.50 (m, 1H, $\underline{H}$-3'); 2.55 (m, 4H, N—C$\underline{H}_2$—CH(OCH$_3$), N—C$\underline{H}_2$—CH$_2$—O); 2.98 (d, J=18.8Hz, 1H, $\underline{H}$-10ax); 3.22 (dd, J=1.0, 18.8Hz, 1H, $\underline{H}$-10e); 3.39 (s, 3H, CH(OC$\underline{H}_3$)); 3.55, 3.95 (two m, 2H, NCH$_2$C$\underline{H}_2$O); 3.70 (m, 1H, $\underline{H}$-4'); 3.95 (m, 1H, $\underline{H}$-5'); 4.09 (s, 3H, C$\underline{H}_3$—O-4); 4.10 (m, 2H, O—C$\underline{H}_2$CONH); 4.50 (m, 1H, NCH$_2$—C$\underline{H}$(OCH$_3$)); 4.67 (s, 2H, C$\underline{H}_2$-14); 5.28 (m, 1H, $\underline{H}$-7); 5.54 (m, 1H, $\underline{H}$-1'); 7.64 (bs, 1H, CO$\underline{NH}$NH$_2$); 7.78 (t, J=7.9Hz, 1H, $\underline{H}$-2); 8.04 (d, J=7.9Hz, 1H, $\underline{H}$-1); 13.32 (s, 1H, O$\underline{H}$-11); 13.98 (s, 1H, O$\underline{H}$-6).

EXAMPLE 4

Preparation of 14-O-[1-(4-carboxy-1-n-butyl)carbamoylmethyloxy-1-cyclohexyl)]-3'-deamino-3'-[2(S)-methoxy-4- morpholinyl]doxorubicin [8', A—O—=13b', b=1, B=—(CH$_2$)$_2$—, R$_1$=R$_2$=H, g=4]

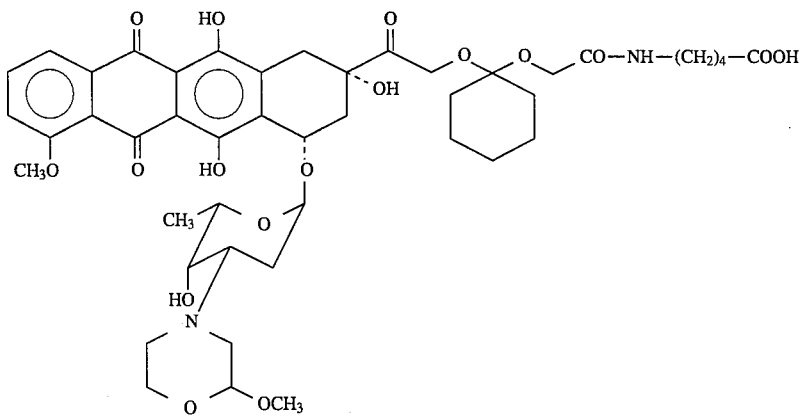

8'

γ-aminobutyric acid (15 mg, 0.15 mmole) was dissolved in 0.05M phosphate buffer pH 7.6 (2.5 ml) and added with compound 4' (30 mg, 0.033 mmole), prepared as described in Example 2, dissolved in acetonitrile (3 ml). The mixture was kept overnight at room temperature, than brought to pH 6 with acetic acid and extracted with n-butanol. The organic layer was separated and evaporated under vacuum. The residue was chromatographed on silicic acid column using as eluting system a mixture of methylene chloride/methanol (95/5 by volume) to afford 20 mg of the title compound 8'. TLC on Kieselgel Plate (Merck) F$_{254}$, eluting system methylene chloride/methanol (95/1 by volume) R$_f$=0.55. MS-FD: m/e 884 (M+).

EXAMPLE 5

Preparation of polyglutamic acic-conjugate of formula 1' [1': A—O—=13b', b=1, B=—(CH$_2$)$_2$—, R$_1$=R$_2$=H, Z=—NH—NH—CO—, a=2, T=poly-L-Glutamic acid]

Poly-L-Glutamic acid, molecular weight 2000–15000 (Sigma) (85 mg) and compound 6' (20 mg) prepared as described in Example 3, were dissolved in dimethylformamide (2 ml) and stirred for three hours. After that, N-ethoxycarbonyl-2-ethoxy-1,2-dihydroquinoline (25 mg) was added. The mixture was kept under stirring overnight, then was poured into a mixture of ethyl ether and petroleum ether. The precipitate was collected on a sintered glass filter, washed with ethyl ether and dissolved with a 2.5% aqueous solution of sodium hydrogen carbonate (8 ml). The solution was passed through a reverse phase column RP-8, 40–63 μm (Merck) (30×1.8 cm) and eluted with a mixture of water and acetonitrile from 0 to 20% of acetonitrile. The elute containing the conjugate was lyophilized then collected on a sintered glass filter, washed with methanol and ethyl ether to give the title compound 1' (45 mg). By spectroscopic evaluation, the conjugate contains 13% of methoxy morpholino of formula 13b.

EXAMPLE 6

Preparation of poly(GluNa,Ala,Tyr)-conjugate of formula 1" [1": A—O—=13b', b=1, B=—(CH$_2$)$_2$—, R$_1$=R$_2$=H, Z=—NH—NH—CO—, a=2, T=poly(GluNa,Ala,Tyr)]

Following the same procedure described in Example 5, Poly(GluNa,Ala,Tyr) (1:1:1), M$_w$ 25000–50000 (Sigma) (60 mg) and compound 6' (20 mg) prepared as described in Example 3, were dissolved in dimethylformamide (2 ml), stirred for three hours and treated with N-ethoxycarbonyl-2-ethoxy-1,2-dihydroquinoline (25 mg), to give, after reverse phase column purification, 35 mg of the title compound 1".

EXAMPLE 7

Preparation of anti-melanoma conjugate of formula 1'" [1'": A—O—=13b', b=1, B=—(CH$_2$)$_2$—, R$_1$=R$_2$=H, Z=—NH—, T=Epl]

A 10$^{-2}$M solution of compound 4', described in Example 2, in N,N-dimethylformamide (37.5 mol) was slowly added to 1 ml of a 2 mg/ml solution of purified mouse monoclonal anti-human melanoma antibody Epl [Giacomini, P. et al., Int. J. Cancer 39 729 (1978] in 0.1M NaH$_2$PO$_4$, 0.1M NaCl, pH 8 at r.t. with stirring. The reaction mixture was stirred overnight at r.t. in the dark and centrifugated. The conjugate was isolated by gel filtration chromatography over a SEPHADEX-G25 column (PD-10, Pharmacia) eluting with PBS (Gibco, 10X, Cat.N.042 -04200M) pH 7.3. The excluded peak was collected (1.5 ml) and assayed for anthracycline content spectrophotometrically at 480 nm. The protein content was assayed with a colorimetric protein analysis (BCA, Pierce). The conjugate contained 1.27 mg/ml of antibody with an anthracycline/protein ratio of 11.4/1.0. The chemico-physical profile of the product was determined by HPLC-gel filtration analysis (BioSil SEC-250 column, 0.1M NaH$_2$PO$_4$, 0.1M NaCl, pH 7.0) with dual wavelength detection (280 and 480 nm) and by SDS-PAGE. By HPLC, a 50% protein aggregate formation was detected, eluting at the column void volume.

By SDS-PAGE, both the anthracycline absorption and the Coomassie-dye protein reaction were located at 160 kD molecular weight, confirming covalent bonds formation and indicating aggregate formation due to non-covalent interaction.

EXAMPLE 8

Preparation of anti-colon carcinoma conjugate of formula 1$^{iv}$ [1$^{iv}$: A—O—=13b', b=1, B=—(CH$_2$)$_2$—, R$_1$=R$_2$=H, Z=—NH—NH—, T=B72.3]

A solution of B72.3 antibody (U.S. Pat. No. 4,522,918) at 2.6 mg/ml in 0.1M NaH$_2$PO$_4$, pH 6 (1 ml) was treated with 0.1 ml of a 0.1M solution of NaIO$_4$ in water at 4° C. in the dark. After 1 h the product was purified by gel filtration chromatography over a SEPHADEX G25 column (PD-10 Pharmacia) eluting with 0.1M NaH$_2$PO$_4$ buffer, pH 6.

The protein containing fraction (1.7 mg, 2 ml) was treated with 30 molar equivalents of a 10% w/v solution of compound 6', described in Example 3, in the same buffer. After 24 h at 37° C. in the dark, the reaction mixture was purified as described in Example 7.

The conjugate contained 0.48 mg/ml of antibody with an anthracycline/protein ratio of 2.4/1, and was 85% monomeric.

EXAMPLE 9

Preparation of copolymer of 3-methacryloylamino-2-hydroxy-propane and 14-O-{1-[4-(N-methacryloylglycylphenylalanylleucylglycyl)hydrazino]-carbonylmethyloxy-cyclohexyl}-3'-deamino-3'[2(S)-methoxy-4-morpholinyl]doxorubicin (1$^v$) [1$^v$: A—O—=13b', b=1, B=—(CH$_2$)$_2$—, R$_1$=R$_2$=H, Z=—NHNH—CO—, T=HPMA X=Gly-Phe-Leu-Gly].

0.58 g of copolymer HPMA [X=Gly-Phe-Lue-Gly, 4.2% (mol/mol %) of P=OC$_6$H$_4$pNO$_2$ content], prepared as described by J. Kopecek et al., Makromol. Chem. 177, 2833–2848 (1976)] by radical polymerization of 3-methacryloylamino-2-hydroxy-propane and 4-nitrophenyl ester of N-methacryloylglycylphenylalanylleucylglycine, was dissolved in dry dimethylsulfoxide (15 ml) with derivative 6' (0.1 g), prepared as described in Example 3. After two days at room temperature, 1-amino-2-propanol (0.4 ml) was added and the reaction mixture was poured in 1/1 (v/v) mixture of acetone and ethyl ether (300 ml). The precipitate was collected and resolved in 95% ethanol (10 ml) from which the title compound 1$^v$ was precipitated from acetone (80 ml), collected and washed with ether.

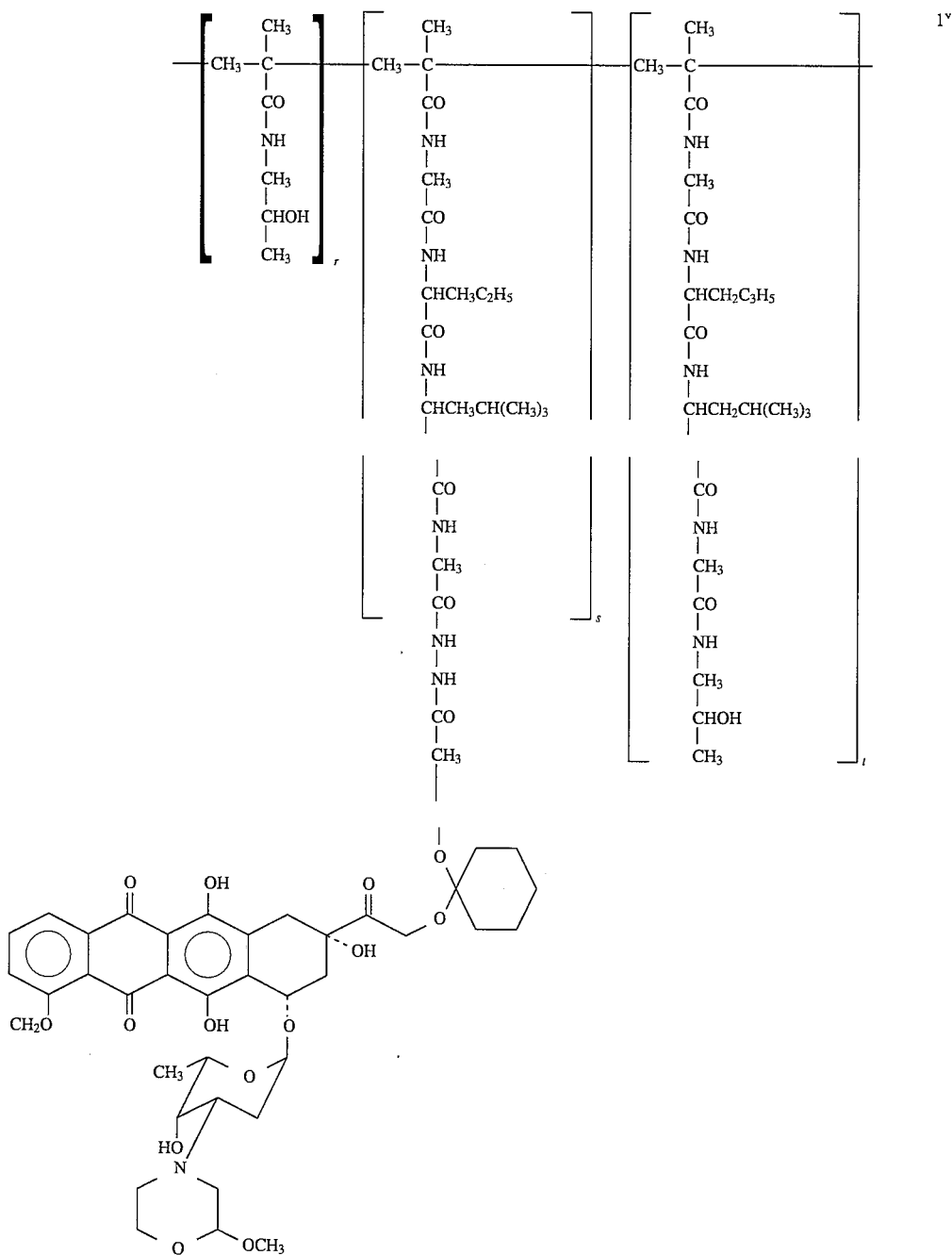

Yield 0.51 g. Content of anthracycline (w/w %) calculated as 3'-deamino-3'[2(S)-methoxy-4-morpholinyl]doxorubicin hydrochloride (13a): 3.3%

% molar ratio in formula $1^v$ (r:s:t)=(95.7:0.79:3.52).

EXAMPLE 10

Preparation of 14-O-(1-piperazinocarbonylmethyloxy-cyclohexyl)-3'-deamino-[2(S)-methoxy-4-morpholinyl]doxorubicin [11', A—O—=13b', b=1, B=—(CH$_2$)$_2$—, R$_1$=R$_2$=H]

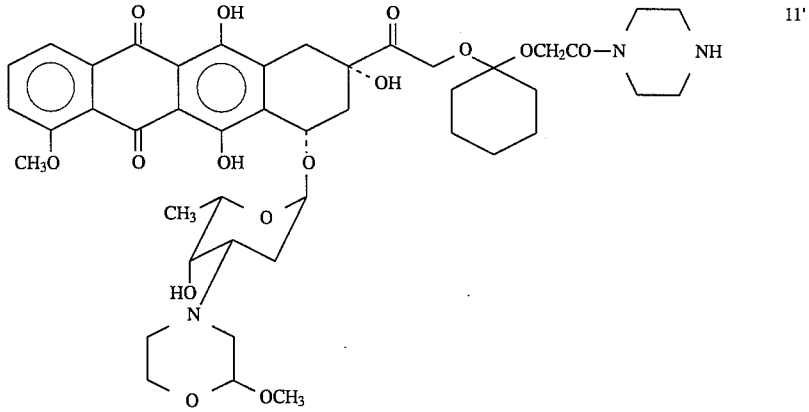

Compound 4 (100 mg), prepared as described in Example 2, was dissolved in anhydrous tetrahydrofurane (20 ml), cooled at 0° C. and added with a solution of piperazine (50 mg) in anhydrous tetrahydrofurane (2 ml). The reaction mixture was stirred at 0° C. for 15 minutes, then was diluted with methylene chloride (100 ml), washed with water (3×50 ml). The organic phase was separated, dried over anhydrous sodium sulphate and the solvent was removed under reduced pressure. The crude product was chromatographed on silicic acid column using as eluting system a mixture of methylene chloride/methanol (80/20 by volume). Compound 11', 80 mg, was precipitated with ethyl ether.

TLC on Kieselgel Plate (Merck) $F_{254}$, eluting system methylene chloride/methanol (70/30 by volume) $R_f$=0.60. FD-MS: m/z 868 (100, [M+H]$^+$)

$^1$HNMR (200 MHz, CDCl$_3$) δ: 1.35 (d, J=6.6Hz, 3H, 5'-CH$_3$); 1.3–1.9 (m, 12H, 2'-CH$_2$, cyclohexane); 2.11 (dd, J=4.2, 14.6Hz, 1H, 8ax-H); 2.3–2.5 (m, 5H, 8eq-H, 3'-H, 3"ax-H, 5"-CH$_2$); 2.60 (dd, J=3.9, 11.2Hz, 1H, 3"eq-H); 2.86 (m, 4H, CH$_2$—NH—CH$_2$); 3.00 (d, J=18.9Hz, 1H, 10ax-H); 3.23 (dd, J=1.2, 18.9Hz, 1H, 10eq-H); 3.37 (s, 3H, 2"-OCH$_3$); 3.4–3.6 (m, 5H, CON(CH$_2$)$_2$, 6"ax-H); 3.90 (m, 1H, 6"eq-H); 3.98 (q, J=6.6Hz, 1H, 5'-H); 4.07 (s, 3H, 4-O CH$_3$); 4.18 (s, 2H, OCH$_2$CON); 4.48 (dd, J=2.5, 3.9Hz, 1H, 2"eq-H); 4.79 (m, 2H, 14-CH$_2$); 5.24 (m, 1H, 7-H); 5.53 (m, 1H, 1'-H); 7.37 (d, J=7.7Hz, 1H, 3-H); 7.76 (dd, J=7.7, 6.8Hz, 1H, 2-H); 8.02 (d, J=6.8Hz, 1H, 1-H); 13.30 (bs, 1H, 11-OH); 13.98 (s, 1H, 6-OH).

EXAMPLE 11

Preparation of copolymer of 3-methacryloylamino-2-hydroxy-propane and 14-O-{1-[4-(N-methacryloylglycyl)piperazin-1yl]carbonylmethyloxy-cyclohexyl}-3'-deamino-3' [2(S)-methoxy-4 -morpholinyl]doxorubicin (1$^{vi}$) [1$^{vi}$: A—O—=13b', b=1, B=—(CH$_2$)$_2$—, R$_1$=R$_2$=H, Z=[1,4-piperazinyl]—CO—, T=HPMA and X=HN—CH$_2$—CO—].

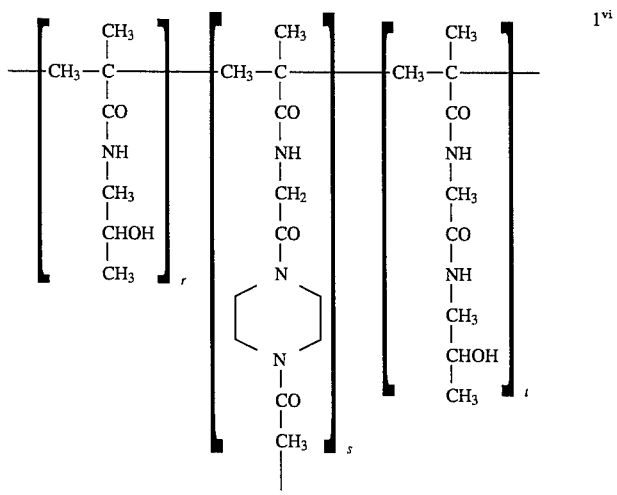

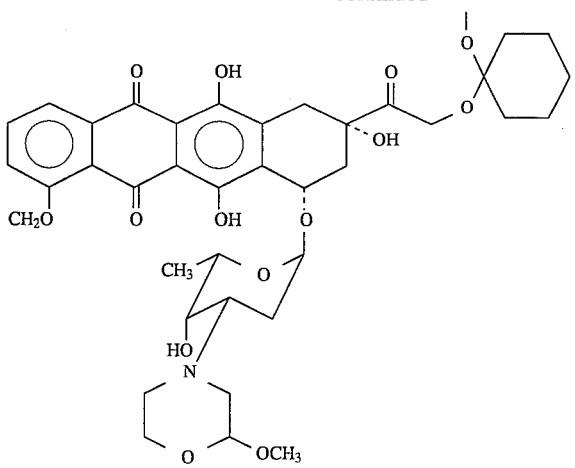

0.42 g of copolymer HPMA [X=HN—CH$_2$—CO—, 7.6% (mol/mol %) of P=OC$_6$H$_4$pNO$_2$ content], prepared as described by J. Kopecek et al., Makromol. Chem. 177, 2833–2848 (1976)] by radical polymerization of 3-methacryloylamino-2-hydroxy-propane and 4-nitrophenyl ester of N-methacryloylglycine, was dissolved in dry dimethylsulfoxide (2.2 ml) and reacted with derivative 11' (0.07 g), prepared as described in Example 10. After two hours at room temperature, 1-amino-2-propanol (0.05 ml) was added and the reaction mixture was poured in 1/1 (v/v) mixture of acetone and ethyl ether (200 ml). The precipitated was collected and resolved in 95% ethanol (10 ml) from which the title compound 1$^{vi}$ was precipitated from acetone (80 ml), collected and washed with ether.

Yield: 0.39 g. Content of anthracycline (w/w %) calculated as 3'-deamino-3'[2(S)-methoxy-4-morpholinyl]doxorubicin hydrochloride (13a); 9.74%

% molar ratio in formula 1$^{vi}$ (r:s:t)=(92.4:2.15:5.45).

EXAMPLE 12

Preparation of copolymer of 3-methacryloylamino-2-hydroxy-propane and 14-O-{1-[4-(6-methacryloylaminocaproyl)piperazin-1yl]-carbonylmethyloxy-cyclohexyl}-3'-deamino-3'[2(S)-methoxy-4-morpholinyl]doxorubicin (1$^{vii}$) . [1$^{vii}$: A—O—=13b', b=1, B=—(CH$_2$)$_2$—, R$_1$=R$_2$=H, Z=[1,4-piperazinyl]—CO—, T=HPMA and X=HN—(CH$_2$)$_2$—CO—].

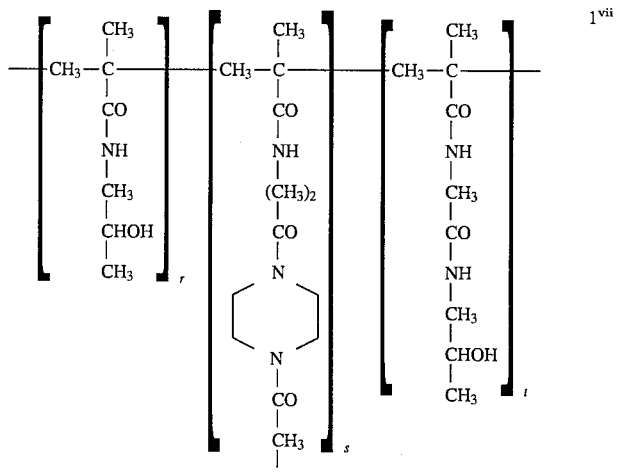

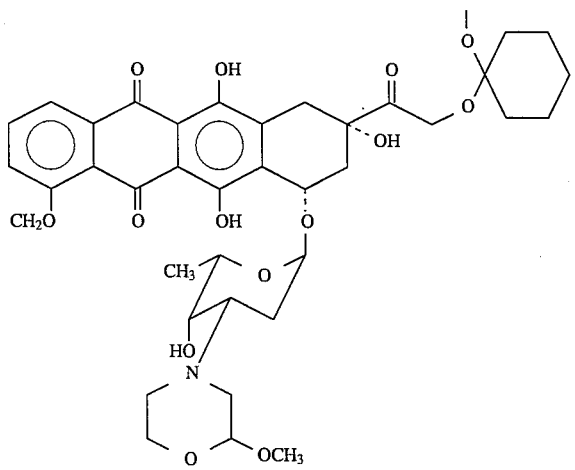

0.6 g of copolymer HPMA [X=HN—(CH$_2$)$_2$—CO—, 5.3% (mol/mol %) of P=OC$_6$H$_4$pNO$_2$ content], prepared as described by J. Kopecek et al., Makromol. Chem. 177, 2833–2848 (1976)] by radical polymerization of 3-methacryloylamino-2-hydroxy-propane and 4-nitrophenyl N-methacryloylaminocapronate, was dissolved in dry dimethylsulfoxide (3 ml) and reacted with derivative 11' (0.1 g), prepared as described in Example 10. After two hours at room temperature, 1-amino-2-propanol (0.1 ml) was added and the reaction mixture was poured in 1/1 (v/v) mixture of acetone and ethyl ether (200 ml). Following the same procedure described in Example 11, 0.58 g of the title compound 1$^{vii}$ was recovered.

Content of anthracycline (w/w %) calculated as 3'-deamino-3'[2(S)-methoxy-4-morpholinyl]doxorubicin hydrochloride (13a): 9.2%

% molar ratio in formula 1$^{vii}$ (r:s:t)=(94.7:2.05:3.31)

EXAMPLE 13

Preparation of conjugate of Poly(Glu-Na,Ala.Tyr) (1:1:1) and 14-O-(1-piperazinocarbonylmethyloxy-cyclohexyl)-3'-deamino-[2(S)-methoxy-4-morpholinyl]doxorubicin (1$^{viii}$) [1$^{viii}$: A—O—=13b', b=1, B=—(CH$_2$)$_2$—, R$_1$=R$_2$=H, Z=[1,4-piperazinyl]—CO—, T=poly(Glu-Na,Ala,Tyr).

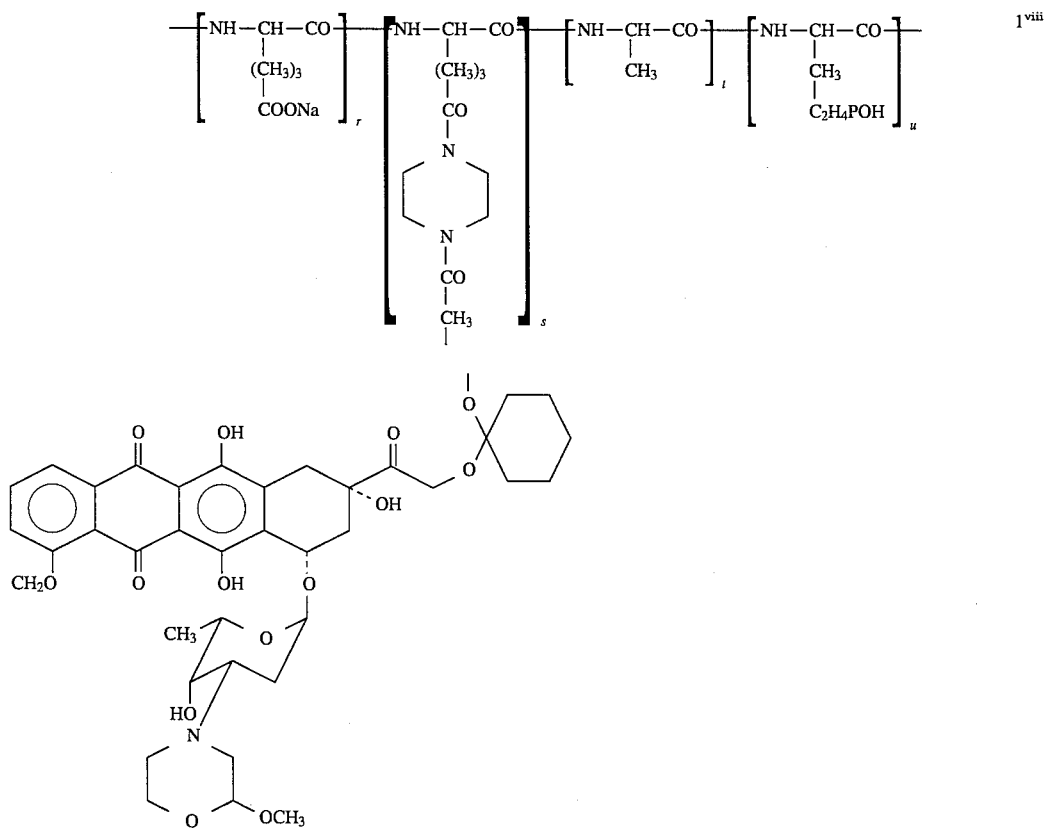

Poly(Glu-Na,Ala,Tyr) (1:1:1) $M_w$ 25000–40000 (Sigma), (0.2 g) was dissolved in water (5 ml) under stirring at room temperature. The corresponding free acid was precipitated from the aqueous solution by acidifying at pH 3 with 0.1N HCl. Poly(Glu-OH,Ala,Tyr) (0.17 g), recovered and dried under vacuum, was dissolved in dry dimethylformamide (10 ml) and added with 14-O-(1-piperazinocarbonylmethyloxy-cyclohexyl)-3'-deamino-[2(S)-methoxy-4-morpholinyl] doxorubicin (11') (0.035 g), prepared as described in Example 10, and N-ethoxycarbonyl-2-ethoxy-1,2-dihydro-quinoline (EEDQ) (0.08 g). Another aliquot of EEDQ (0.08 g) was added after three hours. The reaction mixture was stirred overnight at room temperature, than was poured in ethyl ether (300 ml). The precipitated was suspended in water (10 ml) and treated with 0.1N NaOH (14 ml); the solution was brought to pH 8.5 with 0.1N HCl and passed on a column of Sephadex G10. The aqueous solution was liophilized to give 0.16 g of the title compound $1^{viii}$.

Content of anthracycline (w/w %) calculated as 3'-deamino-3'[2(S)-methoxy-4-morpholinyl]doxorubicin hydrochloride (13a): 10%

% molar ratio in compound of formula $1^{viii}$ (r:s:t:u) (31.33:2.01:33.33:33.33).

We claim:

1. A conjugate of general formula 1:

$$(A\text{—}O\text{—}W\text{—}Z)_a\text{—}T \qquad 1$$

wherein the moiety A—O— is the residue of drug of formula A—O—H in which —O—H is a primary or secondary hydroxyl group; a is an integer of from 1 to 5; W is a group of general formula 2:

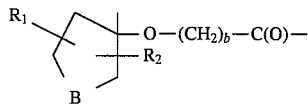

wherein b is an integer of from 1 to 4, B represents a $C_1$-$C_3$ alkylene group and $R_1$ and $R_2$ are each independently selected from the group consisting of hydrogen, a halogen selected from the group consisting of chlorine, bromine and iodine, a $C_1$-$C_4$ alkyl group, phenyl or phenyl substituted by a halogen selected from the group consisting of chlorine, bromine and iodine, or by a $C_1$-$C_4$ alkyl group;

Z is a spacer group selected from the group consisting of:
 (i) —NH—;
 (ii) —NH—$(CH_2)_c$—S—S— wherein c is an integer of from 1 to 4;
 (iii) —NH—$(C)_d$—N=CH— wherein:
  (a) d is 0
  (b) d is 1 and (C) represents —NH—CO—$(CH_2)_e$—CO—NH— in which e is an integer of from 2 to 4;
  (c) d is an integer of from 1 to 4 and (C) represents —$(CH_2)_f$—O—$(CH_2)_f$— in which f is 1 or 2, or
  (d) d is an integer of from 2 to 6 and (C) is $CH_2$;
 (iv) —NH—$(C)_d$—NH—CO— wherein (C) and d are as defined above;
 (v) —(D)—NH— wherein (D) represents —NH—$(CH_2)_g$—CO— in which g is an integer of from 2 to 6;
 (vi) —(E)—CO— wherein (E) represents —NH—$(CH_2)_g$—NH— in which g is an integer of from 2 to 6 and (vii) the piperazinylcarbonyl moiety of the formula

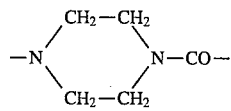

and T is a carrier moiety.

2. A conjugate according to claim 1, wherein the moiety A—O— is derived from an anthracycline of formula A—O—H.

3. A conjugate according to claim 1, wherein the moiety A—O— represents

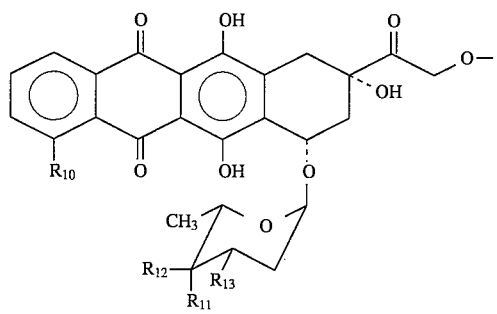

in which $R_{10}$ is a hydrogen atom or a hydroxy or methoxy group, one of $R_{11}$ and $R_{12}$ is a hydrogen atom and the other is a hydroxy group or $R_{11}$ is a hydrogen or iodine atom and $R_{12}$ is a hydrogen atom, and $R_{13}$ is an amino group or represents a nitrogen atom enclosed in a morpholino ring.

4. A conjugate according to claim 1, wherein the carrier moiety T is selected from a polyclonal antibody, or fragment thereof comprising an antigen binding site, capable of binding to a tumor associated antigen; a monoclonal antibody, or fragment thereof comprising an antigen binding site, capable of binding to an antigen preferentially or selectively expressed on tumor cell populations; a peptide or protein capable of preferentially or selectively binding to a tumor cell; and a polymeric carrier.

5. A conjugate according to claim 4, wherein the carrier moiety T is selected from an anti-T-cell antibody, an anti-CD5 antibody, an anti-transferrin receptor antibody, an anti-melanoma antibody, an anti-carcinoma marker antibody, an anti-ovarian carcinoma antibody, an anti-breast carcinoma antibody and an anti-bladder carcinoma antibody.

6. A conjugate according to claim 4, wherein the carrier moiety T is a growth factor.

7. A process for the preparation of a conjugate of formula 1 as defined in claim 1, which process comprises (i) providing a first substance which is able to provide the said spacer group Z and a second substance which is able to provide the said carrier moiety;

(ii) condensing a derivative of formula 3:

$$A\text{—}O\text{—}W\text{—}OH \qquad 3$$

wherein A—O— and W are as defined in claim 1, with the said first substance; and (iii) forming a said conjugate by condensing the product of step (ii) above, or an activated derivative thereof, with the said second substance.

8. A process according to claim 7 in which the condensation is carried out through an activated derivative of the derivative of formula 3 or by direct reaction in the presence of a condensing agent.

9. A process for the preparation of a conjugate of general formula 1 as defined in claim 1, which process comprises (v') condensing a compound of formula 4:

$$A-O-W-L \qquad 4$$

wherein A—O— and W are as defined in claim 1 and L represents an activating group for making an amide linkage, with an amino derivative of formula $H_2N-(CH_2)_g-COOH$ in which g is an integer from 2 to 6, thereby to form a derivative of formula 8:

$$A-O-W-(D)-OH \qquad 8$$

wherein A—O—, W and (D) are as defined in claim 1; optionally converting the compound of formula 8 into an activated derivative of formula 9:

$$A-O-W-(D)-L \qquad 9$$

wherein A—O—, W and (D) are as defined above and L is an activating group for making an amide linkage; and condensing the resultant compound of formula 9 or the compound of formula 8 in the presence of a condensing agent with a substance of formula $T-(NH_2)_x$ wherein T is a carrier moiety and x represents the number of amino groups available for condensation.

10. A process for the preparation of a conjugate of general formula 1, as defined in claim 1, comprising (vi') reacting a compound of formula 4:

$$A-O-W-L \qquad 4$$

wherein A—O— and W are as defined in claim 1 and L represents an activating group for making an amide linkage, with an amino derivative of formula $H_2N-(CH_2)_g-NH_2$ wherein g is an integer from 2 to 6, thereby to form a derivative of formula 10:

$$A-O-W-(E)-H \qquad 10$$

wherein A—O—, W and (E) are as defined in claim 1, or (vii') reacting a compound of formula 4 with piperazine to form a derivative of formula 11:

$$A-O-W-(piperazine)-H \qquad 11$$

and condensing a compound of formula 10 or 11, as above described, with a substance of formula 7:

$$T-(CO-L')_y \qquad 7$$

wherein T is a carrier moiety, y is an integer from 1 to 30 and represents the total number of carboxyl groups on the carrier moiety and L' represents hydroxy or an activating group for making an amide linkage, optionally in the presence of a condensing agent.

11. A process for the preparation of a conjugate of formula 1:

$$(A-O-W-Z)_a-T \qquad 1$$

comprising converting a derivative of formula 3:

$$A-O-W-OH \qquad 3$$

wherein A—O— and W are as defined in claim 1 into an activated derivative of formula 4:

$$A-O-W-L \qquad 4$$

wherein A—O— and W are as defined in claim 1 and L represents an activating group for making an amide linkage, and (i') condensing the resulting compound of formula 4 with a substance of formula $T-[NH_2]_x$ wherein T is a carrier moiety and x represents the number of amino groups available for condensation, or (ii') condensing the compound of formula 4 with a thiol derivative of formula $NH_2-(CH_2)_c-SH$ in which c is an integer of from 1 to 4 and condensing the resultant compound of formula 5:

$$A-O-W-NH-(CH_2)_c-SH \qquad 5$$

wherein A—O—, W and c are as above defined, with a substance of formula $T-[SH]_{x1}$ in which T is as defined above and x1 represents the number of thiol groups available for condensation, or (iii') reacting the compound of formula 4 with hydrazine, a succinic or adipic dihydrazide derivative or a diamino compound and condensing the resultant compound of formula 6:

$$A-O-W-NH-[C]_d-NH_2 \qquad 6$$

wherein A—O—, W, [C] and d are as defined in claim 1, with a substance of formula $T-[CHO]_{x2}$ wherein T is a carrier moiety and x2 represents the number of formyl groups available for condensation.

12. A process for the preparation of a conjugate of formula 1 as defined in claim 1, which process comprises (iv') condensing a compound of general formula 6:

$$A-O-W-NH-[C]_d-NH_2 \qquad 6$$

wherein A—O—, W, [C] and d are as defined in claim 1, with a substance of general formula 7:

$$T-[CO-L']_y \qquad 7$$

wherein T is a carrier moiety, y is an integer from 1 to 30 and represents the total number of carboxyl groups on the carrier moiety and L' represents hydroxy or an activating group for making an amide linkage, optionally in the presence of a condensing agent.

13. A conjugate of the formula 1:

$$(A-O-W-Z)_a-T \qquad 1$$

wherein the moiety A—O— is an antitumor agent selected from the group consisting of an anthracycline derivative, a 3'-deamino-3'-morpholinyl anthracycline derivative which is unsubstituted or substituted at position 2" of the morpholino ring with $C_{1-4}$ alkoxy groups, a pyrimidine analog, a vinca alkaloid derivative, a podophyllotoxin or an illudine; an antiviral agent selected from the group consisting of 3'-azido-3'-deoxy-thymidine (AZT), bromovinyldeoxy-uridine (BVDU), 9-((2-hydroxyethoxy)methyl)guanine (acyclovir) or 9-((1,3-dihydro-2-propoxy)methyl)guanine (gancyclovir); or an antibiotic selected from the group consisting of thienamycin or a penam derivative;

W is a group of the formula 2:

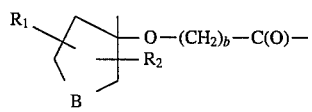

wherein B represents a $C_{1-3}$ alkylene group, $R_1$ and $R_2$ each independently represent hydrogen, halogen, $C_{1-4}$ alkyl, phenyl, a $C_{1-4}$ alkyl substituted phenyl or a halogen substituted phenyl; and b is an integer of from 1 to 4;

Z is
(i) —NH—;
(ii) —NH—(CH$_2$)$_c$—S—S— wherein c is an integer of from 1 to 4;
(iii) —NH—(C)$_d$—N=CH— wherein:
   a) d is 0,
   b) d is 1 and (C) represents —NH—CO(CH$_2$)$_e$—O—NH— wherein e is an integer of from 2 to 4,
   c) d is an integer of from 1 to 4 and (C) represents —(CH$_2$)$_f$—O—(CH$_2$)$_f$— wherein f is 1 or 2, or
   d) d is an integer of from 2 to 6 and (C) is CH$_2$;
(iv) —NH—(C)$_d$—NH—CO— wherein (C) and d are as defined above;
(v) —(D)—NH— wherein (D) represents —NH—(CH$_2$)$_g$—CO— wherein g is an integer of from 2 to 6;
(vi) —(E)—CO— wherein (E) represents —NH—(CH$_2$)$_g$—NH— wherein g is an integer of from 2 to 6 or
(vii) a piperazinylcarbonyl moiety of the formula:

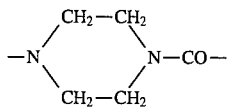

a is an integer from 1 to 30; and

T is a member moiety selected from the group consisting of a polyclonal antibody, or fragment thereof comprising an antigen binding site, capable of binding to a tumor associated antigen; a monoclonal antibody, or fragment thereof comprising an antigen binding site, capable of preferentially or selectively binding to a tumor cell, and a polymeric carrier.

14. A pharmaceutical composition comprising a pharmaceutically acceptable carrier or diluent and, as active ingredient, a conjugate as claimed in claim 1.

15. A derivative of formula 3:

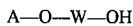    3 wherein A—O— and W are as defined in claim 1.

16. A process for the preparation of a derivative of formula 3:

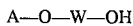    3 which process comprises condensing a drug of formula A—O—H wherein A—O is as defined in claim 1 with a compound of formula 12:

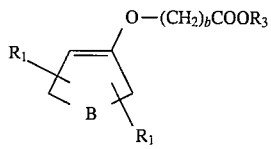    12 wherein B, b, R$_1$ and R$_2$ are as defined in claim 1 and R$_3$ represents a protecting group; and removing the said protecting group from the compound thus formed.

17. A derivative of formula 4:

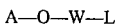    4 wherein A—O— and W are as defined in claim 1 and L represents an activating group for making an amide linkage.

18. A process for the preparation of a derivative of formula 4:

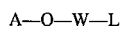    4 wherein A—O— and W are as defined in claim 1 and L represents an activating group for making an amide linkage, which process comprises converting a derivative of formula 3:

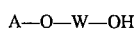

wherein A—O— and W are as defined in claim 1 into a said derivative of formula 4.

19. A derivative of formula 5:

    5 wherein A—O— and W are as defined in claim 1 and c is an integer of from 1 to 4.

20. A process for the preparation of a derivative of formula 5:

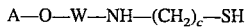    5 wherein A—O— and W are as defined in claim 1 and c is an integer of from 1 to 4, which process comprises converting a derivative of formula 3:

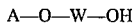    3 wherein A—O— and W are as defined in claim 1, into an activated derivative of formula 4:

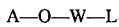    4 wherein A—O— and W are as defined in claim 1 and L represents an activating group for making an amide linkage, and condensing the compound of formula 4 with a thiol derivative of formula NH$_2$—(CH$_2$)$_c$—SH in which c is an integer of from 1 to 4.

21. A derivative of formula 6:

    6 wherein A—O—, W, (C) and d are as defined in claim 1.

22. A process for the preparation of a derivative of formula 6:

    6 wherein A—O—, W, (C) and d are as defined in claim 1, which process comprises converting a derivative of formula 3:

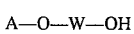    3 wherein A—O— and W are as defined in claim 1, into an activated derivative of formula 4:

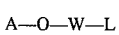    4 wherein A—O— and W are as defined in claim 1 and L represents an activating group for making an amide linkage, and reacting the compound of formula 4 with hydrazine, a succinic or adipic dihydrazide derivative or a diamino compound.

23. A derivative of formula 9:

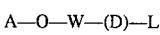    9 wherein A—O—, W and (D) are as defined in claim 1 and L is an activating group for making an amide linkage.

24. A process for the preparation of a derivative of formula 9:

A—O—W—(D)—L    9 wherein A—O—, W and (D) are as defined in claim 1 and L is an activating group for making an amide linkage, which process comprises condensing a compound of formula 4:

A—O—W—L    4 wherein A—O— and W are as defined in claim 1 and L represents an activating group for making an amide linkage, with an amino derivative of formula $H_2N$—$(CH_2)_g$—COOH in which g is an integer from 2 to 6, thereby to form a derivative of formula 8:

A—O—W—(D)—OH    8 wherein A—O—, W and (D) are as defined in claim 1; and converting the compound of formula 8 into the activated derivative of formula 9.

25. A derivative of formula 10 or 11:

A—O—W—(E)—H    10

A—O—W—(piperazine)—H    11 wherein A—O—, W and (E) are as defined in claim 1.

26. A process for preparing a derivative of formula 10 or 11:

A—O—W—(E)—H    10

A—O—W—(piperazine)—H    11 wherein A—O—, W and (E) are as defined in claim 1, which process comprises converting a derivative of formula 3:

A—O—W—OH    3 wherein A—O— and W are as defined in claim 1, into an activated derivative of formula 4:

A—O—W—L    4 wherein A—O— and W are as defined in claim 1 and L represents an activating group for making an amide linkage, and reacting the compound of formula 4 with an amino derivative of formula $H_2N$—$(CH_2)_g$—$NH_2$ wherein g is an integer of from 2 to 6, thereby to form the derivative of formula 10, or reacting the compound of formula 4 with piperazine, thereby to form the derivative of formula 11.

* * * * *